United States Patent [19]
Lazarus

[11] Patent Number: 5,693,088
[45] Date of Patent: Dec. 2, 1997

[54] INTRALUMINAL VASCULAR GRAFT

[76] Inventor: Harrison M. Lazarus, 853 Thirteenth Ave., Salt Lake City, Utah 84103

[21] Appl. No.: 485,004

[22] Filed: Jun. 7, 1995

Related U.S. Application Data

[63] Continuation-in-part of Ser. No. 149,040, Nov. 8, 1993, abandoned.

[51] Int. Cl.⁶ .............................. A61F 2/06; A61M 29/00
[52] U.S. Cl. .................... 623/1; 623/12; 606/195
[58] Field of Search .................... 623/1, 11, 12; 606/194, 195, 151, 152, 153, 191, 196, 197, 198; 600/36

[56] References Cited

U.S. PATENT DOCUMENTS

| | | |
|---|---|---|
| 3,818,511 | 6/1974 | Goldberg .............................. 606/153 |
| 4,140,126 | 2/1979 | Choudhury . |
| 4,355,426 | 10/1982 | MacGregor . |
| 4,562,596 | 1/1986 | Kornberg . |
| 4,577,631 | 3/1986 | Kreamer . |
| 4,617,932 | 10/1986 | Kornberg . |
| 4,776,337 | 10/1988 | Palmaz . |
| 5,104,399 | 4/1992 | Lazarus . |
| 5,123,917 | 6/1992 | Lee . |
| 5,151,105 | 9/1992 | Kwan-Gett . |
| 5,282,824 | 2/1994 | Gianturco . |
| 5,376,118 | 12/1994 | Kaplan et al. .............................. 623/11 |
| 5,397,345 | 3/1995 | Lazarus . |
| 5,405,379 | 4/1995 | Lane . |

*Primary Examiner*—Debra S. Brittingham
*Attorney, Agent, or Firm*—Trask, Britt & Rossa

[57] ABSTRACT

An intraluminal vascular graft is structure to be deployable within a vessel for incorporation therein without use of hooks or barbs. The intraluminal vascular graft structure comprises a tubular body formed of a biocompatible material and a frame structure, having both circumferential support and longitudinal support structures, which support the graft at a distal end thereof and upwardly from the distal end. The vascular graft also includes a porous collar which have sufficient porosity to promote and enhance ingrowth of tissue and other materials into the porous collar from the surrounding vessel environment, thereby facilitating incorporation of the intraluminal vascular graft into the vessel wall. The tubular body of the intraluminal vascular graft may include one or more leg portions suitable for repairing bifurcated vessels which, in conjunction with the circumferential and longitudinal support structures, and the porous collar, assure positioning and support of the vascular graft within the vessel and against the crotch of the bifurcation. The intraluminal vascular graft is designed to form a tight seal between the graft and inner vessel wall, especially at the upstream end of the graft, to prevent perigraft leakage and formation of pseudoaneurysms around the graft.

22 Claims, 5 Drawing Sheets

INTRALUMINAL VASCULAR GRAFT

RELATED APPLICATIONS

This application is a continuation-in-part of Ser. No. 149,040, filed Nov. 8, 1993, now abandoned the contents of which are incorporated herein by reference.

BACKGROUND OF THE INVENTION

1. Technical Field

This invention relates to medical devices in general, and specifically to grafts positionable intraluminally for repairing aneurysms or other vascular defects in humans and animals.

2. Background

Aneurysms are caused by weakening of a vessel wall which results in the outward ballooning of the wall under the pressure of flowing blood. Aneurysms are more prevalent in men than in women, and are more common with advancing age. Prior to the development of technology to repair the bulging blood vessel, aneurysms posed a fatal threat to those who developed them. Even with the early development of repair procedures, significantly invasive surgery was required to access the aneurysm. Today, graft structures have been developed which allow insertion and delivery of the graft to the point of the aneurysm using less invasive procedures.

Known intraluminal graft structures generally comprise a tubular graft, expansion means for deploying and positioning the graft in the vessel and anchoring or attachment means for keeping the graft in place within the vessel. Many varying types of expansion means have been disclosed, including those described in U.S. Pat. No. 4,140,126 to Choudhury; U.S. Pat. No. 4,776,337 to Palmaz; U.S. Pat. No. 5,123,917 to Lee; and U.S. Pat. No. 5,151,105 to Kwan-Gett. Means have also been described for providing longitudinal support to the graft, including those means described in U.S. Pat. No. 4,562,596 to Kornberg and U.S. Pat. No. 5,151,105 to Kwan-Gett.

Additionally, various means for attaching the graft to the vessel have been disclosed. Most frequently, hook, barb or pin means are described and used, including the means described in U.S. Pat. No. 4,140,126 to Choudhury; U.S. Pat. No. 4,562,596 to Kornberg; and U.S. Pat. No. 5,151,105 to Kwan-Gett. In some instances, the hook or barb means are attached to the expandable means as described in U.S. Pat. No. 4,140,126 to Choudhury and U.S. Pat. No. 5,104,399 to Lazarus. U.S. Pat. No. 4,577,631 to Kreamer discloses use of an adhesive covering the entire outside of the graft to provide adherence of the luminal intima to the graft.

The most commonly used intraluminal graft structures have hooks or barbs which pierce into or through the wall of the vessel to anchor the graft to the vessel above the aneurysm. That is, most, if not all, currently described intraluminal grafts are supported in the vessel upstream from or above the disease condition. However, hooks or barbs may damage the vessel, particularly where the vessel is weakened already by an aneurysm or other disease condition. Additionally, there are instances when the condition of the vessel may make it impossible or imprudent to use a graft device having hooks or pins, such as the existence of calcium deposits. Such conditions may also limit the usefulness of adhesives.

A further problem encountered with graft devices currently in use is the leakage of blood around the upstream end of the graft. Leakage occurs, and blood fills the aneurysmal sac, because gaps form between the graft and the inner wall of the vessel, usually at the upstream end of the graft device. Most failures of vascular grafts are due to leakage, and the patient's condition is compromised. Devices have been described in the literature which address, to some extent, the problem of leakage around the graft device. Examples of such devices are described in U.S. Pat. No. 5,282,824 to Gianturco and U.S. Pat. No. 5,405,379 to Lane. However, such devices do not assure a tight seal between the graft and the vessel wall while meeting the other necessary characteristics of a vascular graft suitable for implantation in badly damaged vessels, or vessels which have an unusual morphology.

Thus, it would be advantageous to provide an intraluminal graft which is adapted for use in vascular repair under any conditions, but particularly under conditions which limit or prevent the use of intraluminal grafts having hook, pin, barb or staple attachment means. Further, it would be advantageous to provide an intraluminal graft which is structured to be easily implanted, even under conditions of severe vascular damage and/or aberrant morphology, and which is incorporated into the internal vessel wall to assure a complete seal between the extreme ends of the graft and the vessel wall thereby preventing leakage.

DISCLOSURE OF THE INVENTION

In accordance with the present invention, an intraluminal vascular graft is structured to facilitate incorporation of at least a portion of the graft into the internal vessel wall of a damaged or aneurysmal vessel, either at the extremities of the graft or along a substantial portion of the graft, to prevent leakage of blood around the graft and into the damaged portion of the vessel. The intraluminal vascular graft is further structured to be radially expandable to engage the inner wall of the vessel upon deployment and to be supported within the vessel from a position downstream from, or below, a disease condition existing in the vessel. The intraluminal vascular graft is structured to be flexible along the longitudinal axis of the graft to facilitate deployment through non-linear vessels and to render the graft suitable for implantation in vessels which are non-linear. While the intraluminal vascular graft of the invention may be used in any number of various vascular repairs, it is particularly suitable in the repair of aneurysms of the abdominal aorta, which is one of the most common types of aneurysm.

The intraluminal graft of the present invention generally comprises a biocompatible tube, a radially expandable frame attached to the biocompatible tube, flexible longitudinal support structure to position the graft within the vessel and to provide support for the biocompatible tube and non-puncturing attachment means for incorporating the graft into the internal wall of the vessel in a manner to prevent perigraft leakage. As used herein, perigraft leakage means flow or leakage of blood between the graft and the internal wall of the vessel such that blood fills the aneurysmal sac surrounding the graft.

The biocompatible tube of the present invention is capable of being compressed to provide a graft having a reduced circumferential dimension to permit insertion of the graft into a vessel (e.g., femoral artery) for transportation to the disease site of a vessel. The tube is thereafter capable of expanding radially outwardly from a central longitudinal axis to provide a close fit between the tube structure and the inner vessel wall. The tube has at least two open ends- one which may be termed a proximal end, and one which may be termed a distal end. As used herein, "proximal" refers to the end of the graft which is positioned upstream, or which is oriented toward the cranium of the patient. As used herein, "distal" refers to the end of the graft which is positioned downstream, or which is oriented toward the caudal end of the patient. The tube may be made of any suitable biocompatible material or materials, including polyester (e.g., Dacron®) and polytetrafluoroethylene.

When used in vessels which bifurcate, such as the abdominal aorta, the tube may include leg portions which extend into one or more branching vessels resulting from the bifurcation. The tube may have a single leg portion extendable into a single branching vessel. More suitably, however, the tube has two leg portions extendable into both branching vessels. The relative lengths of the two leg portions may be equal, or one may be longer than the other as dictated by the particular condition of the vessel. The leg portions facilitate positioning and support of the device in bifurcated vessels by providing a crotch area between the two leg portions which straddles the crotch or cusp between the branching vessels of the bifurcation.

In an alternative embodiment, the tube may have a single leg portion with a hole formed in the tube opposite the leg portion to allow fluid flow into the other branching vessel. In another alternative embodiment, the tube may have a single leg portion with no corresponding opening in opposing position, or the tube may have a first leg portion and a second leg portion, the shorter leg portion having no opening therein to allow blood flow therethrough. An intraluminal vascular graft of such construction would be useful in repairing bifurcated vessels (such an iliac artery) where the surgeon specifically desires to restrict blood flow to a single branching vessel of the bifurcation.

The tube of the intraluminal vascular graft may also comprise a single tube, having no extending leg portions, which is suitable for repairing less complex vessel structures or disease conditions. In a single tube configuration, the intraluminal vascular graft includes only a proximal open end and a distal open end to allow movement of blood through the graft.

The intraluminal vascular graft further includes expandable circumferential support structures which, immediately upon deployment of the graft, radially expand to the full inner circumferential dimension of the vessel to be repaired. Radial expansion of the circumferential support structures positions the tubular graft securely against the internal wall of the vessel upon deployment. The expandable circumferential support structures are secured at the proximal end of the tube and at the distal end of the tube. The expandable circumferential support structure positioned at the distal end of the graft tube, also referred to herein as the expandable caudal support, provides a means for positioning the graft tube within the vessel and for supporting the graft within the vessel at a point distal, or downstream, to the disease condition. In bifurcated vessels, the expandable caudal support is particularly structured to provide support and seating of the graft tube at the point where the vessel bifurcates, or on what is otherwise termed the cusp of the bifurcation.

Circumferential support structures may also be secured to the terminal ends of the leg portions when the graft is constructed with extending leg potions. The circumferential support structures thus assure positioning of the leg portions against the inner wall of the branching vessels into which the leg portions extend, and anchor the leg portions thereagainst.

Placement of the circumferential support structures at the proximal end and distal end of the tube render the graft suitable for placement in a vessel which is non-linear. In other words, while most vessels tend to be substantially straight, or only slightly curved, other vessels may bend or kink due to aberrant morphology of the vessel or to positioning of the vessel in proximity to other organs. Such vessels may have as much as a ninety-degree angle of curvature. Diseases or aneurysms which occur in such vessels present a unique challenge to repair techniques. The present invention is particularly constructed to accommodate the repair of vessels under those unique circumstances by being longitudinally flexible and capable of bending to meet the angle of the vessel.

The expandable circumferential support structures may be constructed of any material, or may take any form, which provides the ability of reducing the circumferential dimension of the circumferential support structures prior to deployment of the intraluminal graft, and which allows the structures to expand once the graft is deployed. The expandable circumferential support structures may preferably be instantaneously self-expanding, and to that end may be formed, for example, as a tensioned ring of flexible material which unwinds or decompresses upon release of a compression force surrounding the circumferential support structures. Alternatively, the expandable circumferential support structures may be expandable by unrelated means, such as by an inflatable angioplasty balloon introduced following insertion of the graft.

The intraluminal vascular graft also includes at least two adjustable longitudinal support structures oriented along the length of the biocompatible tube and positioned at an angle to the expandable circumferential support structures. The angle between the longitudinal support structures and the circumferential support structures may be anywhere from about sixty to about one hundred and twenty degrees, but may preferentially be substantially perpendicular to each other. The longitudinal support structures maintain the tube in its full, predetermined length following deployment within the vessel, and prevent collapse of the tube upon itself. By "predetermined" is meant that the length of the longitudinal support structures and graft tube which is required to repair the vessel may be determined by known x-ray or fluoroscopic techniques, and prior to insertion, the surgeon may select a graft of appropriate dimension or may modify or adjust the longitudinal support structures and graft tube to fit the vessel. The longitudinal support structures support the graft longitudinally within the vessel and act in tandem with the expandable caudal support to support the graft in the vessel from the distal end of the graft upward.

The longitudinal support structures also maintain the graft in place and function to keep the graft from moving back and forth longitudinally within the vessel. The longitudinal support structures facilitate prevention of migration of the graft within the vessel. Orientation and anchoring of the graft within the vessel is facilitated by longitudinal support structures extending beyond the proximal or upstream end of the biocompatible tube. The longitudinal support structures are most suitably flexible so that they may bend in a direction transverse the longitudinal axis of the tube, such as may be necessary when the graft is deployed in a vessel which bends along its course as previously described. The longitudinal support structures, in an alternative embodiment, may be further adjustable after the graft is placed within the vessel. Such adjustability may be provided, for example, by use of longitudinal support structures having telescoping members.

The expandable circumferential support structures and the adjustable longitudinal structures generally comprise what may be called the frame of the graft structure. The frame is secured to the biocompatible graft tube by any suitable means, such as tacking or sewing the frame to the tube, or by weaving the frame into the tube. The frame may be positioned within the graft tube material so that the frame is exposed to fluid moving through the graft tube. Alternatively, and more suitably, the frame is disposed on the outer surface of the graft tube material and is, therefore, positioned between the inner vessel wall and the outer surface of the graft tube.

To facilitate placement of the graft within the vessel, some portion of the frame may be treated with radio-opaque materials which are detectable by fluoroscopic or other appropriate methods. Most suitably, at least one of the longitudinal structures may be treated with radio-opaque materials to detect correct positioning and correct twisting of the intraluminal vascular graft upon deployment within the vessel.

Fixed attachment of the graft tube to the interior of the vessel, or the intima, is provided by non-puncturing attachment means secured to the outer surface of the biocompatible tube. The attachment means extend about, or encircle, the full outer circumference of the tube at the proximal or upstream end of the tube to provide complete contact between the intraluminal vascular graft and the circumference of the inner surface of the vessel positioned proximate the attachment means. Complete contact between the attachment means and the inner circumferential surface of the vessel at the upstream end prevents perigraft leakage. Attachment means may also be positioned at or near the distal end of the graft tube to enhance incorporation of the graft into the vessel.

The attachment means is made of a flexible material which renders it suitable for compression prior to deployment and expandable again upon deployment to extend to the full circumferential dimension of the inner surface of the vessel. The material of the attachment means is formed from material which is, or is otherwise treated to be, porous and/or textured to promote the attachment or ingrowth of tissue into the attachment means thereby incorporating at least a portion of the intraluminal vascular graft into the vessel.

When reference is made herein to "ingrowth of tissue and other matter" it should be noted that the internal environment of a damaged vessel may present a variety of tissue and other cellular matter, including vascular tissue, fibroblasts, clotted blood, platelets and other deposited matter. The attachment means of the present invention are designed to encourage the filling of the pores in the material of the attachment means with either tissue or other cellular material from the surrounding environment to form a mechanical securement with the attachment means. Eventually, some vascularized tissue, as well as scar tissue, will form in and about the attachment means to fully incorporate the graft into the damaged vessel.

The attachment means may be made of a material which has inherent porosity, such as polypropylene, polyurethane, latex or other suitable material, or combinations of material, which renders at least the surface of the attachment means suitable for ingrowth of tissue and matter. As used herein "porous" means that openings are formed on at least the surface of the material facing outwardly toward the interior of the vessel. As such, "porous" may include materials which have dimples or depressions positioned on the surface thereof, closed-cell pores which extend partially through the thickness of the material, open-cell pores which form a channel through the thickness of the material, and both regularly- and irregularly-shaped and sized pores. The attachment means may thus be formed from material having the requisite porosity to enhance ingrowth of matter, or the attachment means may be formed from a material lacking porosity which is then coated or treated with a material providing the surface with the requisite porosity (e.g., metal coated with latex).

The attachment means may also be treated, such as by coating or infusion, with a substance or material which promotes attachment of the vessel to the graft. Such substances may promote healing or ingrowth of tissue into the attachment means and may include, for example, fibrinogen or plasma treated in absence of ammonia. The attachment means may also include, or be treated with, a radio-opaque material in the manner described previously to facilitate deployment and correct positioning of the intraluminal vascular graft within the vessel.

The attachment means of the present invention may, in a first embodiment, comprise a collar of material which surrounds the entire circumference of certain portions of the biocompatible tube. At a minimum, a first collar having porosity and texture sufficient to promote ingrowth of tissue and matter is positioned about the proximal, or upstream, end of the intraluminal vascular graft to assure incorporation of the graft into the surrounding vessel thereby preventing perigraft leakage. A second collar having porosity and texture may be positioned about the distal, or downstream, end of the intraluminal vascular graft to facilitate complete attachment of the device to the vessel. Additionally, a collar of the described material may be positioned about each leg of the tube when the biocompatible tube is configured with one or more leg portions. The collars may suitably be positioned proximate the expandable circumferential support structures so that upon deployment of the intraluminal vascular graft the radially expanding circumferential support structures urge the collars of the attachment means securely against the inner surface of the vessel. The collars may, however, be positioned at some distance from the frame structures as may be dictated by the particular conditions of deployment or vascular repair.

In an alternative embodiment, the attachment means may be a toroidal collar having an internal inflatable space which facilitates expansion of the intraluminal vascular graft to contact the inner surface of the vessel. The use of a toroidal collar as attachment means may be particularly suitable in diseased vessels where the vessel wall is significantly stretched and/or distended as compared to the normal shape or patency of the vessel. The ability of the toroidal collar to enlarge, and thus expand outwardly from the surface of the biocompatible tube to contact the vessel, enables the intraluminal vascular graft to adjust to the unique internal dimension or shape of the vessel and to encourage ingrowth of tissue into the attachment means. In other words, the toroidal collar presents an anisotropic wall oriented toward the interior of the vessel. At a minimum, a toroidal collar is positioned about the proximal end of the biocompatible tube. However, additional toroidal collars may be positioned about the distal end of the tube and/or about the extremity of each leg portion in embodiments configured with leg portions.

In yet another embodiment, the attachment means may comprise a toroidal encasement member having an internal and inflatable space. The toroidal encasement member extends from proximate the proximal end of the biocompatible tube to the distal end of the tube, and is positioned on the outer surface of the tube, between the biocompatible tube and the inner circumference of the vessel. The internal and enlargeable space of the toroidal encasement member allows the attachment means to extend outwardly from the biocompatible tube and to contact the inner surface of the vessel. This embodiment is particularly suitable for use in diseased vessels where the vessel wall is stretched and/or distended because the toroidal encasement member can expand to contact the inner surface of the vessel and thereby encourage incorporation of the entire vessel into the entire length of the graft between the proximal end and distal end of the vascular graft.

The toroidal collar or toroidal encasement member may be made of any suitable biocompatible material which encourages ingrowth of tissue and other matter into the attachment means, including, for example, polyurethane. The toroidal or toroidal encasement member may be formed from an inherently porous material or may be made of a non-porous material treated to render the surface porous and textured to facilitate ingrowth of tissue thereinto.

The toroidal collars or toroidal encasement member are enlarged or inflated following deployment of the graft in the vessel. A conduit is connected to each toroidal collar or to the toroidal encasement member through which fluid may be introduced into the internal space of each toroid. The conduit connected to each toroidal collar or toroidal encasement member extends from the attachment means to outside the patient's body where flow of fluid through the conduit and into the toroidal collar or toroidal encasement member may be controlled. Any suitable fluid may be introduced into the internal space of the attachment means, be it liquid or gas, but saline solution is particularly suitable. Once the toroidal collars or toroidal encasement member is enlarged to the desired degree, the conduit is detached from the attachment means, whereupon a valve means is caused to close and seal off the internal space of the attachment means. The pressure of the enlarged toroidal collar or toroidal encasement member must not exceed the mean arterial blood pressure (MABP) in order to avoid rupture. Yet, when deployed in the aorta, the pressure of the enlarged toroidal collar or toroidal encasement member must be greater than that of the lumbar arteries which apply pressure to the aorta. If deployed in a vessel having a non-linear profile, it is preferable that the toroidal encasement member be sufficiently deflated to permit the intraluminal vascular device to curve or bend in conformance with the shape of the vessel.

To further attach the intraluminal vascular graft to the vessel, the biocompatible tube may be coated or otherwise treated with a material or substance which induces an inflammatory response, such as polylactic acids, polyglycolic acids or polyamino acids. The graft tube may also be constructed or treated in a manner which encourages ingrowth of tissue on to the graft tube to enhance or promote incorporation of the tube into the surrounding vascular environment, along with the attachment means. Such treatment may include coating or infusing the tube material with collagen, for example.

Also, the longitudinal and/or circumferential support structures may be constructed of a material which inherently causes an inflammatory response and/or which is constructed of a material which promotes ingrowth of tissue into the support structure. The longitudinal and/or circumferential support structures may also be treated, such as by coating with collagen, polylactic acids, polyglycolic acids or polyamino acids to promote ingrowth of the device into the surrounding vascular tissue.

The intraluminal graft is delivered to the site of the diseased vessel by transport means which are sized and structured to contain the intraluminal graft therein or thereabout, and which facilitate insertion of the device through the arterial system. A particularly suitable transport means comprises a capsule within which the intraluminal graft is retained in a collapsed condition, and deployment means for releasing the intraluminal graft from the capsule and positioning it within the vessel.

The capsule is flexibly structured to navigate smoothly through the tortuous pathway that can often be encountered in the arterial tree. The capsule and associated deployment structures, described hereafter, are inserted into a small incision made in an artery or vein located remotely from the area of diseased vessel. With respect to aortic aneurysms, for example, the capsule is inserted into a femoral artery and passed upwardly to the abdominal aorta. A guide wire may be used initially to determine proper placement. The capsule containing the graft may then be threaded about or over the guide wire to the point of deployment.

When the capsule has reached the disease site, a deployment structure deploys the device within the vessel. Expansion actuator means may be included if necessary, such as an angioplasty balloon, to facilitate expansion of the device. Alternatively, the deployment structure may be structured with expansion actuator means to both deploy and facilitate expansion of the graft. Exemplar deployment means include a hydraulic force.

In a first suitable implantation method, the capsule containing the compressed graft is inserted into the diseased vessel. A guide wire may be used to insert the capsule. Once positioned at the site of deployment, a positioning means maintains the graft in place while the capsule is withdrawn from the vessel. Alternatively, the capsule may be removed from about the graft structure, such as when the capsule is in the form of a tear-away sheath. The graft may be assisted in deployment from the capsule by means of a stabilizer rod which is manipulable from outside the patient's body.

An angioplasty balloon may be used, if necessary, to assist in deploying and expanding the graft. Alternatively, the graft may be deployed from the capsule by application of a hydraulic force provided by infusion of saline solution. Once the graft is released from the capsule, the compressive forces which kept the frame of the graft positioned within the capsule are released and the graft expands outwardly from a central axis of the graft. The capsule and other deployment structures are retrieved from inside the vessel by withdrawing those structures over the inserted guide wire. Use of hydraulic means to deploy the graft reduces the amount of deployment structures required for deployment, and insertion is possible through a smaller incision.

When deployed in a vessel, the radially expandable circumferential support structures may spring open to expand the tube within the vessel. Radial expansion of the tube is ideally instantaneous and complete (i.e., the graft expands to the full inner circumferential profile of the vessel so that the attachment means contact the inner surface of the vessel). However, expansion may be assisted with additional expansion means.

The longitudinal support structures maintain the graft in an elongated expansion within the vessel. The expandable distal support and the longitudinal structures maintain the graft in position within the vessel at the distal or downstream end of the vessel. When deployed in a bifurcating vessel, like the abdominal aorta, the expandable distal support comes to rest upon the cusp of the bifurcation to support the graft. The longitudinal support structures are forced radially outwardly from a central axis of the graft by force of the expandable distal support, and the longitudinal support structures aid in expansion of the graft.

After the graft has been deployed and extended radially outwardly to the full inner circumferential profile of the vessel, the attachment means contact the inner surface of the vessel. The porosity of the attachment means, in addition to any treatment with a substance which promotes healing and ingrowth of tissue, initiates incorporation of the device into the surrounding vessel environment. The pressure of the circumferential support structures against the attachment means at the proximal end of the graft provides a comprehensive seal between the graft and the vessel. Where appropriately treated, an immediate inflammatory response is initiated between the graft and the inner surface of the vessel. Attachment of the graft to the vessel wall may be completed within a few days to weeks after insertion of the graft. While ingrowth continues and the vascular graft becomes more incorporated into the vessel wall, the frame structure of the graft keeps the graft in place and fully supported within the vessel.

When the biocompatible tube is structured with leg portions, the leg portions are deployed in generally the same manner as described previously. If one leg portion is used, that leg portion is typically deployed within the iliac artery through which the deployment structures are passed. When two leg portions are used, the deployment of the second leg may be accomplished in different ways. For example, the second leg portion may be folded up against the outer surface of the graft prior to deployment. With proper positioning of the graft, the second leg portion will naturally extend into the appropriate vessel bifurcation by the flow of blood through the graft.

In alternative deployment means, a catheter or guide wire may be inserted into the other femoral artery (which was not used for insertion of the vascular graft) prior to insertion of the device into the femoral artery. The guide wire or catheter may be inserted until the distal end (the end inserted into the vessel) reaches the point of bifurcation. The distal end of the guide wire can then be passed across the bifurcation and down through the other artery (through which deployment of the device will take place) until the distal end of the guide wire or catheter can be retrieved from the other artery to outside the patient's body. The distal end of the guide wire or catheter may then be sutured to the leg portion of the device which will ultimately be positioned in the other iliac artery. The entire intraluminal vascular graft is then inserted into the femoral artery and through the iliac artery until positioned within the aorta. Following deployment of the entire graft tube within the aorta, the guide wire, catheter or suture attached to the second leg portion is retrieved from the other femoral artery. As a result, the second leg is brought over to the other iliac artery into position. The guide wire, catheter or suture is then removed from the other artery.

In an alternative procedure, the guide wire or catheter passed through the other femoral artery may be passed across the bifurcation and manipulated until the distal end of the guide wire or catheter encounters the second leg portion of the graft tube. The distal end of the guide wire or catheter may be configured with a hook or other similar device for attaching the second leg portion thereto. Once the second leg portion is engaged by the distal tip, the guide wire or catheter may be retrieved from the vessel thereby causing the second leg portion to be brought over to the other branching vessel. The guide wire or catheter may then be removed from the artery.

The intraluminal vascular graft of the present invention is designed to repair atherosclerotic aneurysms (i.e., calcified and containing large amounts of thrombotic material). The intraluminal vascular graft is structured to be sufficiently flexible to navigate through tortuous arterial systems, and thereby avoid dislodging laminated clotting and grumous material in the aneurysmal sac. Dislodgement of such material can cause embolisms and is to be avoided. Further, the presently disclosed graft is designed to mold and adhere to calcification within the vessel and to heal to irregular aortic surfaces.

BRIEF DESCRIPTION OF THE DRAWINGS

In the drawings, which illustrate what is currently considered to be the best mode for carrying out the invention.

DETAILED DESCRIPTION OF THE DRAWINGS

Figure 1:
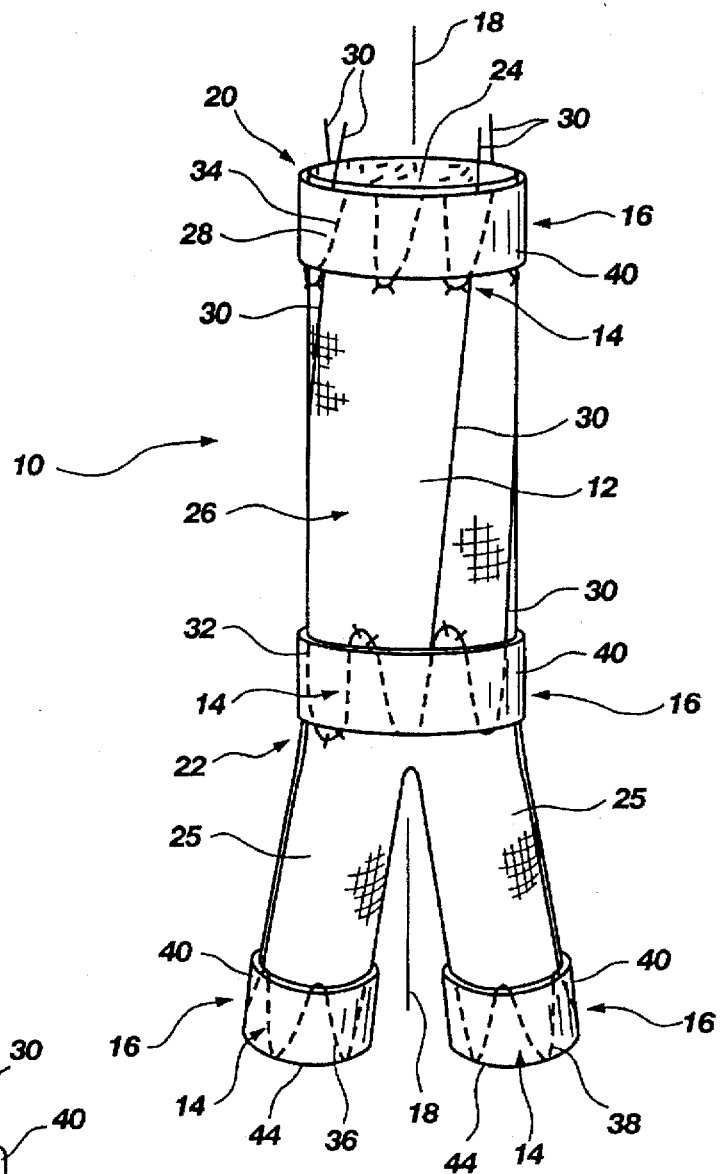
FIG. 1 is a view in elevation of a first embodiment of the intraluminal vascular graft illustrating the attachment means as a circumferential collar.

FIG. 1 illustrates a first embodiment of the intraluminal vascular graft 10 of the present invention which generally comprises a biocompatible tubular body 12, a frame structure 14 and attachment means 16. More specifically, the tubular body 12 is formed from a biocompatible material which has the ability to be manipulated into a tube of smaller circumferential dimension relative to a longitudinal axis 18 formed through the tubular body 12. The ability to be manipulated to a circumferentially smaller dimension allows the tubular body 12 to be positioned within a transportation means sized to fit within a vessel lumen. By "tubular" is meant a body having a lumen, but it is understood that the cross section of the tubular body 12 may be round or any other suitable shape or geometry.

The tubular body 12 has a first open proximal end 20 which is oriented upstream in the vessel. When placed in the abdominal aorta, the proximal end 20 of the graft 10 is oriented toward the cranial end of the patient. The tubular body 12 also has an open distal end 22 which is oriented downstream in the vessel. When positioned in the abdominal aorta, the distal end 22 is oriented caudally to the patient. A lumen 24, or passageway, is formed between the proximal end 20 and the distal end 22 for movement of blood therethrough.

Figure 2:
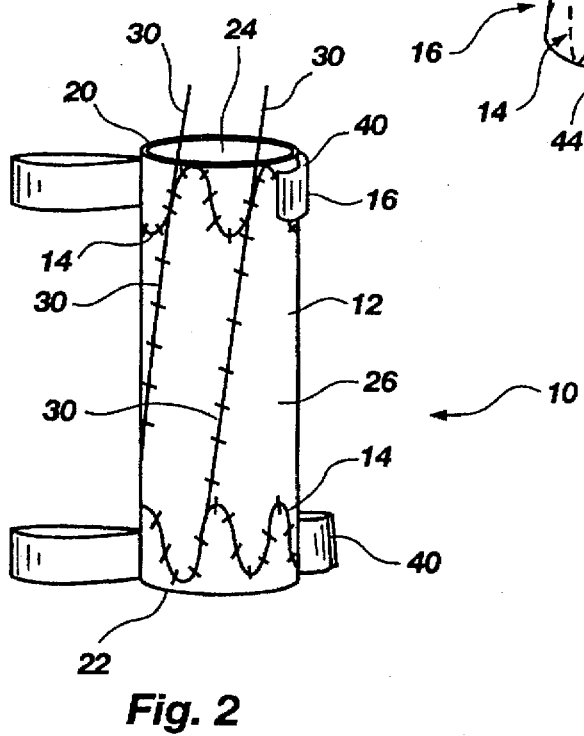
FIG. 2 is a view in elevation of a simplified version of the first embodiment where the tubular body of the graft has no leg portions, and the attachment means are shown partially separated from the tubular body.

The tubular body 12 may be simply a tube with an open proximal end 20 and an open distal end 22, as illustrated in FIG. 2. Alternatively, as illustrated in FIG. 1, the tubular body 12 may include one or more tubular leg portions 25 which extend into the branching vessels of a bifurcated vessel. This configuration may be particularly suitable for repairing the abdominal aorta which branches into the left and right iliac arteries.

The tubular body 12 may be formed from any suitable biocompatible material, including polyester or polytetrafluoroethlyene. Additionally, the outer surface 26 of the tubular body 12 may be treated with a substance or material which causes an inflammatory response, or otherwise encourages ingrowth of tissue and other matter from the surrounding vessel environment into the surface 26 of the tubular body 12.

The frame 14 of the intraluminal vascular graft 10 generally comprises circumferential support structures 28, as shown in FIG. 2 (shown in phantom positioned below the attachment means 16 in FIG. 1), which provide support of the distal end 20 of the vascular graft 10 and provide substantially instantaneous radial expansion to the tubular body 12 upon deployment. The frame 14 also includes a plurality of longitudinal support structures 30 which extend along the length of the tubular body 12 for supporting the tubular body 12 in a fully extended state upon deployment. The circumferential support structures 28 and longitudinal support structures 30, in tandem, function to provide support to the vascular graft 10 from the distal end 22 upward.

The circumferential support structures 28 have a determined maximum circumferential dimension when deployed in the vessel. The determined maximum circumferential dimension approaches the inner circumferential dimension of the vessel in which the graft is deployed. The circumferential support structures 28 are made in any configuration, or of any material, which renders the structures capable of being manipulated to present a smaller circumferential dimension relative to the longitudinal axis 18. The configuration or material of the support structures renders the circumferential support structures 28 capable of expanding radially outward from the longitudinal axis 18 to a circumferential dimension approaching the determined maximum when the vascular graft 10 is deployed.

The circumferential support structures 28 include an expandable distal, or caudal, support 32 and an expandable proximal, or cranial, support 34. Additionally, in the configuration illustrated in FIG. 1, a circumferential support 36, 38 (shown in phantom positioned below the attachment means 16) may be associated with each leg portion 25, and may be positioned at the extremity of the leg portion 25. The circumferential support structures 28 illustrated herein are sine-wave in configuration, but may be of any suitable configuration or construction, including those embodiments illustrated in pending application Ser. No. 149,049, the contents of which are incorporated herein by reference.

The longitudinal support structures 30 may be attached to the circumferential support structures 28, and may particularly be secured to the distal support 32 in a manner which allows the longitudinal support structures 39 to articulate with and move relative to the distal support 32. Although illustrated in FIG. 1 as being connected to one circumferential support structure (distal) 32, the longitudinal support structures 30 may be connected to both the proximal support 34 and the distal support 32.

The longitudinal support structures 30 of the frame 14 extend along the length of the tubular body 12 and support the tubular body 12 in a fully extended form when deployed. The longitudinal support structures 30 also serve to limit longitudinal movement of the graft once deployed in the vessel. The circumferential and longitudinal support structures may be secured directly to the outer surface 26 of the tubular body 12, such as by suturing or sewing, as illustrated in FIG. 2. Alternatively, the longitudinal support structures 30 may be positioned in pockets (not shown) or channels formed on the surface of the tubular body 12, rather than being secured to the circumferential support structures 28. Attachment of the longitudinal support structures 30 to the expandable circumferential support structures 28 may more read fly facilitate deployment and positioning of the longitudinal support structures 30, however.

The frame 14 is shown in FIGS. 1 and 2 as being positioned on an outer surface 26 of the tubular body 12, such that the frame 14 is positioned between the tubular body 12 and the inner wall of the vessel. However, the frame 14 may be positioned, alternatively, within the tubular body 12 so that the frame 14 is exposed to fluid moving through the passageway 24. The frame 14 will be described throughout this disclosure as being positioned on the outside of the tubular body 12, but the disclosed structure and function of the frame 14 is equally applicable, with minor modification, to being positioned within the tubular body 12.

The length of the longitudinal support structures 30 is predetermined by the surgeon prior to the vascular graft 10 being inserted into the patient. A measurement of the area and length of the vascular disease (e.g., aneurysm) is made by means well known in the art, such as by x-ray or fluoroscopic techniques. Once the measurement is taken, the proximal end 20 of the vascular graft 10 may be modified by various means to provide the proper length of vascular graft 10 for implantation. Alternatively, the surgeon may select the appropriate length of graft 10 from inventory.

The frame 14, comprising the circumferential support structures 28 and the longitudinal support structures 30, is made of a suitable material, or of an appropriate construction, to provide flexibility to the frame 14, and particularly to provide flexibility to the longitudinal support structures 30. That is, the graft 10 may bend to substantially a ninety degree angle within a vessel, as the morphology of the non-linear vessel dictates. Flexibility of the frame 14 not only aids in deploying the vascular graft 10, but assists in insertion of the device when fed into a tortuous arterial system, or when deployed in a vessel which, as a matter of course, has a significant bend therein. The frame 14 may, for example, be made of 0.012 inch diameter stainless steel wire with a tensile strength of 277,000 psi (pounds per square inch). Exemplar materials which may be used for constructing the frame include 0.014 inch nitinol, Eligiloy® or MP35®. The circumferential support structures 28 of the frame, and particularly the longitudinal support structures 30, may be treated with radio-opaque substances which are detectable external to the patient's body to facilitate proper deployment and positioning of the graft 10.

Figure 5:
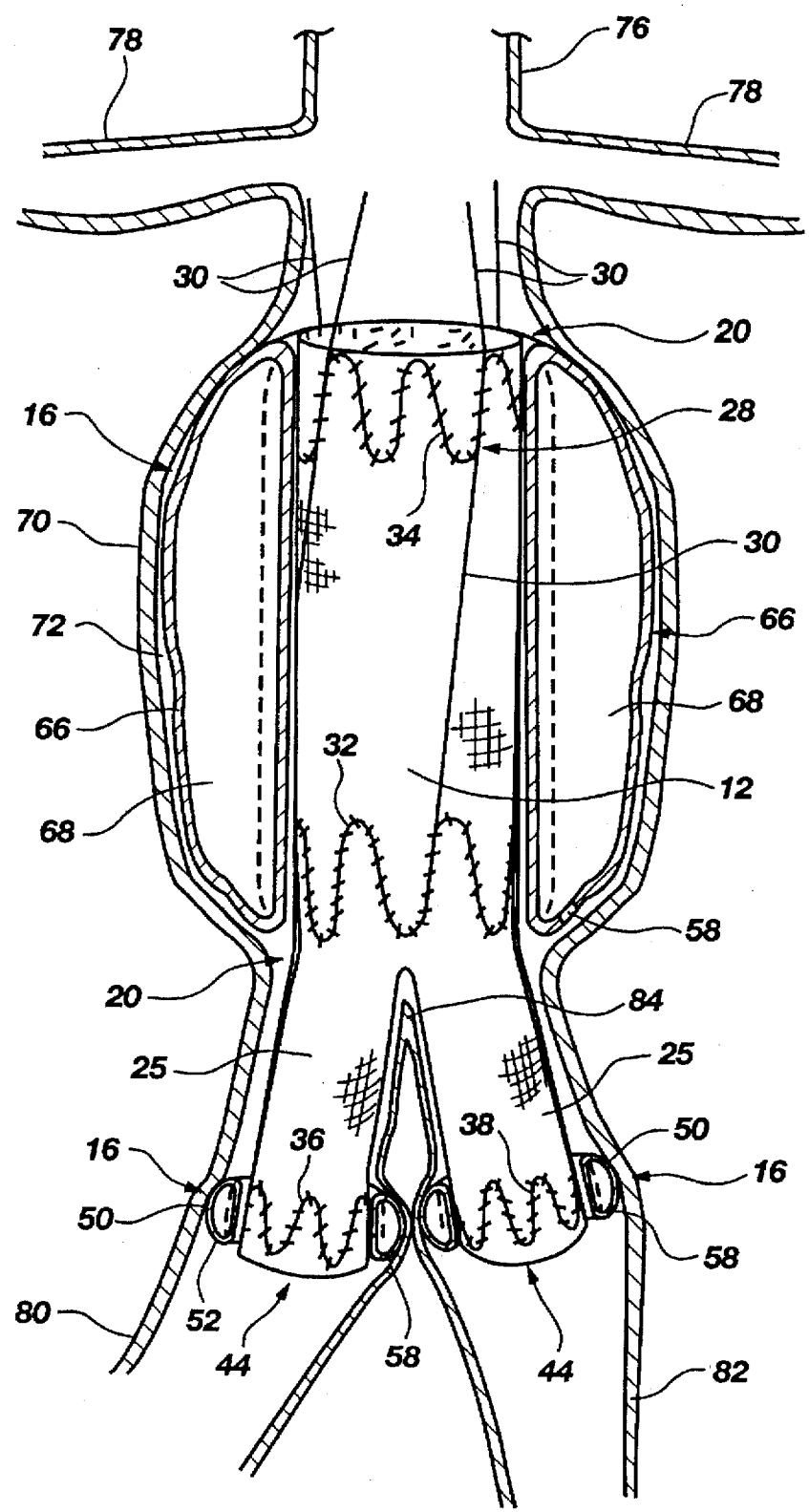
FIG. 5 is a view in elevation of a third embodiment of the intraluminal vascular graft deployed within a bifurcated vessel and illustrating the attachment means as a toroidal encasement member, shown in partial cutaway.

In cases, as previously described, where the area of healthy vessel is shortened near branching vessels, making attachment of the vascular graft difficult, it may be desirable to provide at least two longitudinal support structures 30 which extend beyond the proximal end 20 of the tubular body 12, as shown in FIG. 1. The extended longitudinal support structures 30, when the device is properly deployed, extend above the point of attachment of the graft 10 to the wall of the vessel and extend above the branching vessels. However, the extending longitudinal support structures 30 do not occlude, obstruct or otherwise interfere with the branching vessels (e.g., renal arteries) (FIG. 5).

The vascular graft 10 is supported within the vessel by the circumferential support structures 28 and longitudinal support structures 30 as previously described. Further, attachment of the vascular graft 10 to the inner wall of the vessel is accomplished, in part, by expansion of the circumferential support structures 28 against the inner vessel wall. Attachment of the vascular graft 10 to the vessel is also accomplished by providing attachment means 16 which extend outwardly from the tubular body 12 and contact the inner surface of the vessel wall to form a seal therebetween.

The attachment means 16 are constructed to promote healing and ingrowth of the tissue and other matter into the attachment means 16 from the inner vessel environment to assure a complete seal between the graft 10 and the inner vessel wall. Thus, the attachment means 16 may suitably be made of a material which promotes the ingrowth of tissue and other matter into the material. Examples of such materials are polypropylene, certain polyurethanes, latex, and other biocompatible materials. Suitable materials for use in forming the attachment means 16 are those selected to be porous and/or textured sufficient to promote ingrowth of tissue and other matter. The attachment means may also be made of a material which is less suitable for promoting ingrowth of tissue and other matter from the surrounding vessel environment, but the material of the attachment means 16 is thereafter treated with a material or substance which does render the attachment means 16 porous and textured for ingrowth of tissue and matter.

The attachment means 16 may also be treated or fabricated with substances or materials which promote healing. As used herein, "healing" means to promote the attachment and incorporation of tissue and other materials into the attachment means. The attachment means 16 may be treated with, or may be fabricated with, suitable substances, such as antigenic protein solutions, including fibrinogen, fibronectin, collagen, serum albumin or other plasma treated in absence of ammonia. Fibrinogen, for example, associated with the attachment means 14, causes platelet activation and adherence of neutrophils and macrophages. The fibrinogen triggers thrombosis, and an acute or chronic healing response results in the sealing of the graft 10 to the vessel wall. Xenogeneic proteins (i.e., derived from non-human species or other than the host) may also be used to coat the attachment means to promote host reactivity to the graft 10.

The attachment means 16 may also be treated with radio-opaque substances to provide detection of the graft 10 external to the patient's body to facilitate proper deployment and positioning.

In the embodiment of the device illustrated by FIG. 1, the attachment means 16 is in the form of a collar 40 which surrounds the circumference of the tubular body 12 and is positioned on the outer surface 26 thereof. At a minimum, a collar 40 is positioned about the proximal end 20 of the tubular body 12, oriented at the upstream end of the vessel, to assure a complete seal between the circumference of the graft 10 at the proximal end 20 and the vessel wall so that perigraft leakage does not occur. As illustrated in FIG. 1, the collar 40 attached at the proximal end 20 of the tubular body 12 is positioned over the circumferential proximal support 34. A second collar 40 may be positioned about the distal end 22 of the tubular body 12, and in a similar fashion may be positioned over the circumferential distal support 32. Positioning the collar 40 over a circumferential support structure 28 urges the collar 40 into contact with the inner wall of the vessel as the circumferential support structure 28 radially expands. However, the collars 40 may be positioned at a distance from the circumferential support structures 28.

The collars 40 at the proximal end 20 and distal end 22 of the tubular body 12 assure implantation of the graft 10 into the vessel wall. The placement of the collars 40 in FIG. 1 has the added advantage of enhancing the flexibility of the graft 10 within the vessel because the graft 10 is anchored securely at either end of the disease site in the vessel while still being bendable in the area between the proximal end 20 and the distal end 22.

In a simplified embodiment of the graft 10 where the tubular body 12 comprises only an open proximal end 20 and an open distal end 22, as illustrated in FIG. 2, the placement of collars 40 at the proximal end 20 and distal end 22 is most suitable. When the tubular body 12 includes tubular leg portions 25, as shown in FIG. 1, collars 40 may be positioned about the downstream, or lower, extremity 44 of the leg portions 25. As before, the collars 40 may be positioned about the circumferential support structures 36, 38 attached to each leg portion 25. Collars 40 positioned about the tubular leg portions 25 encourage attachment of the graft 10 within the branching vessels diverging from a bifurcated vessel.

Figures 3, 4:
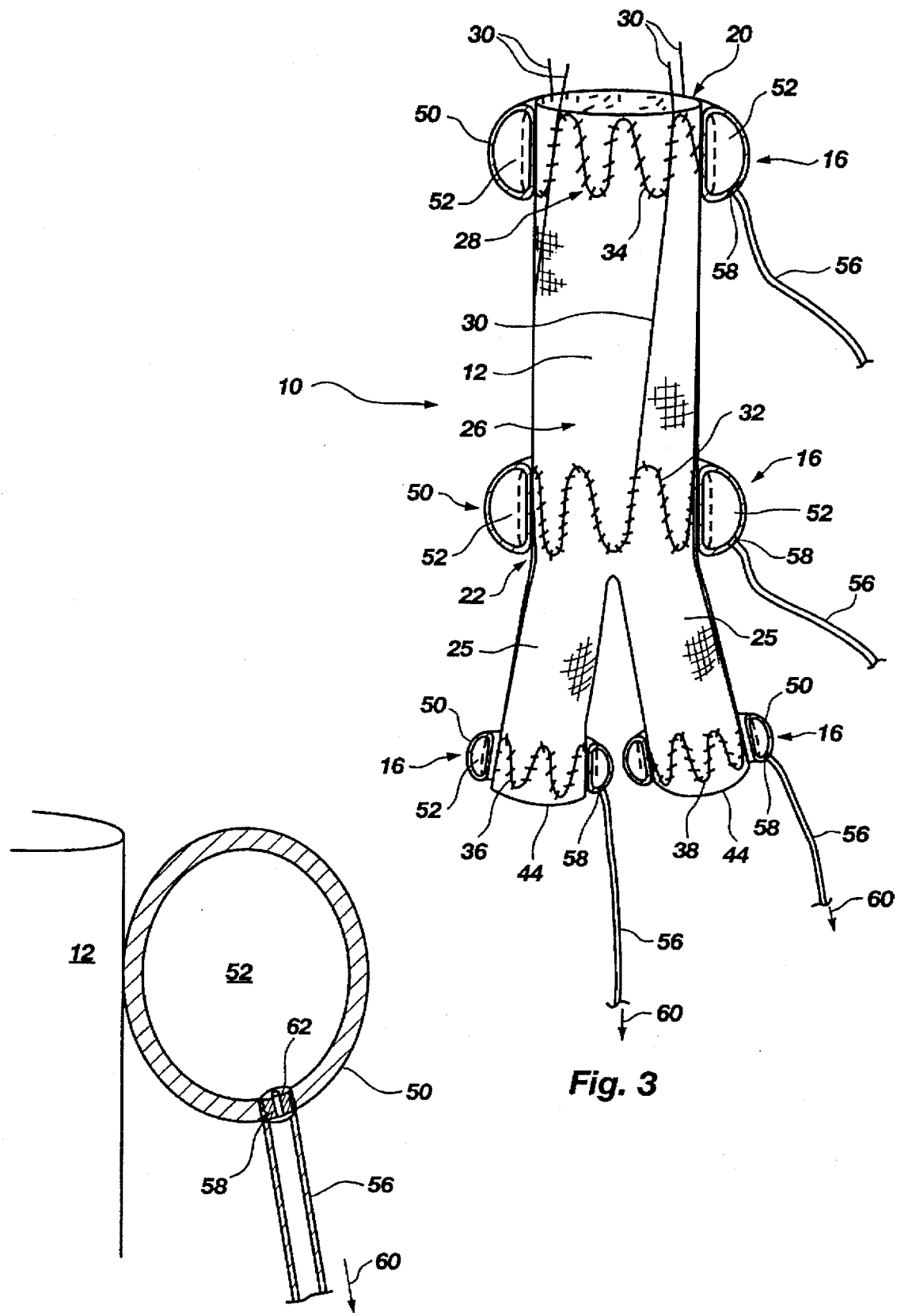
FIG. 3 is a view in elevation of a second embodiment of the intraluminal vascular graft illustrating the attachment means as a toroidal collar, shown in partial cutaway.
FIG. 4 is an enlarged view of a section of a toroidal collar illustrating a sealable valve and inflation line attached thereto.

A second embodiment of the invention is illustrated in FIG. 3 where the attachment means 16 are in the form of toroidal collars 50 having an internal, inflatable space 52 formed therein. The toroidal collars 50 of the illustrated embodiment have the added advantage of being inflatable so that the attachment means 14 extends well beyond the outer surface 26 of the tubular body 12 to contact the inner vessel wall to assure a comprehensive seal between the graft 10 and the vessel wall. This embodiment is particularly suitable for use in vessels where distension has occurred in the vessel due to the disease condition.

The toroidal collar 50 is compressible, along with the tubular body 12, to facilitate deployment of the graft 10 within a vessel. The toroidal collar 50 is thrust outwardly to come into contact with the inner wall of the vessel as the expandable proximal support 34 radially expands. The toroidal collar 50 is thereafter inflated or enlarged to assure a seal between the attachment means 16 and the vessel wall.

At a minimum, a toroidal collar 50 is attached at the proximal end 20 of the tubular body 12, upstream from the diseased area of the vessel. The toroidal collar 50 surrounds the circumference of the tubular body 12. It is important that a seal be formed between the toroidal collar 50 and the vessel at the proximal end 20 of the tubular body 12 to prevent perigraft leakage. In addition, a toroidal collar 50 may be positioned about the circumference of the distal end 22 of the tubular body 12 to assure a seal between the lower end of the tubular body 12 and the inner wall of the vessel, especially where the graft 10 comprises merely an open proximal end 20 and an open distal end 22 (i.e., without leg portions 25).

The existence of toroidal collars 50 at the proximal end 20 and distal end 22 of the graft 10 effectively isolates the diseased portion of the vessel, prevents blood from flowing into the aneurysmal sac, and promotes attachment of the vessel wall to at least the attachment means 16 of the graft 10. Treatment of the tubular body 12 with substances that promote an inflammatory response encourages attachment of the vessel wall to the tubular body 12 as well.

In embodiments of the graft 10, as shown in FIG. 3, where leg portions 25 are formed at the distal end 22 of the graft 10, toroidal collars 50 may be attached at the lower extremities 44 of the leg portions to facilitate anchoring and incorporation of the leg portions 25 into the branching vessels of a bifurcated vessel, such as the iliac arteries branching from the abdominal aorta. Again, the toroidal collars 50 surrounding the circumference of the lower extremities 44 of the leg portions 25 may preferably be positioned over the circumferential support structures 36, 38 of the leg portions 25 which assures contact between the attachment means 16 and the inner vessel wall.

Following deployment of the graft 10 within the vessel, as more fully described hereafter, the toroidal collars 50 may be enlarged or inflated by the introduction of, for example, a fluid into the internal space 52 of each toroidal collar 50. The toroidal collars 50 may be inflated in any number of suitable ways. For example, fenestrations (not shown) may be formed through the wall of the tubular body 12, in alignment with a toroidal collar 50, thereby providing means for flow of blood into the internal space 52 of the toroidal collar 50 to fill or inflate the toroidal collar 50 with blood.

Another example of a means for inflating the toroidal collars 50 with a fluid, from external the patient's body, is illustrated in FIGS. 3 and 4 where an inflation conduit 56 is attached via a closeable valve 58 to the toroidal collar 50. Each inflation conduit 56 extends from the toroidal collar 50 to which it is attached to external the patient's body (indicated by arrow 60 in FIG. 4). The valve 58 includes as opening 62 therethrough, as best seen in FIG. 4, which provides passage of a fluid from the inflation conduit 56 into the internal space 52 of the toroidal collar 50. A fluid, such as gas or, preferably, a saline solution, is pumped through the inflation conduit 56 from extends the patient's body until the toroidal collar 50 is sufficiently inflated to assure a tight seal between the attachment means 16 and the vessel wall. The inflation conduit 56 may then be removed from the valve 58, such as by pulling or gently turning the inflation conduit 56 to dislodge it from the valve 58. Upon removal of the inflation conduit 56, the valve automatically closes sealing the fluid within the internal space 52 of the toroidal collar 50. The inflation conduits 56 attached to each inflated toroidal collar 50, are then removed from the vessel and from the patient's body.

Another alternative embodiment of the present invention is illustrated in FIG. 5 where the attachment means 16 surrounding the tubular body 12 from the proximal end 20 to the distal end 22 is a toroidal encasement member 66 having an internal space 68 which is enlargeable or inflatable. As illustrated in FIG. 5, this embodiment is particularly suitable for repair of aneurysms where the vessel wall 70 is stretched or distended due to disease condition. The ability to inflate the toroidal encasement member 66 allows the attachment means 16 to substantially fill the aneurysmal sac 72, thereby assuring contact between the toroidal encasement member 66 and the inner vessel wall 70. Contact between the toroidal encasement member 66 and the vessel wall 70 promotes healing and ingrowth of tissue and other material into the attachment means 16 thereby facilitating incorporation of the graft 10 into the vessel wall 70.

The graft 10 illustrated in FIG. 5 is deployed within the diseased vessel such that the proximal end 20 of the graft 10 is positioned upstream from the diseased portion of the vessel wall 70. When implanted within the abdominal aorta 76, as shown, deployment is typically below the renal arteries 78 which branch off from the abdominal aorta 76. The longitudinal support structures 30, part of which extend beyond the proximal end 20 of the tubular body 12, help orient and support the graft 10 in place within the vessel, and do not obstruct the openings to the renal arteries 78. The abdominal aorta 76 bifurcates into the right and left iliac arteries, 80, 82. A cusp 84 is formed at the bifurcation of the aorta 76. The distal end 22 of the tubular body 12 is positioned at the cusp 84 and is supported thereon by the circumferential distal support 32. The longitudinal support structures 30 maintain the graft 10 at its full length. Tubular leg portions 25 are illustrated in this embodiment, and a single leg portion 25 is disposed in each of the right and left iliac arteries, 80, 82. The leg portions 25 straddle the cusp 84 of the bifurcation. It is understood that although two leg portions 25 are illustrated in FIG. 5, the present embodiment may be configured with only one leg portion 25 or no leg portions.

Upon deployment, the circumferential support structures 28 radially expand to force the proximal end 20 and distal end 22 of the tubular body 12 outwardly toward the vessel wall 70. Some portion of the toroidal encasement member 66 will contact the vessel wall 70, particularly in those portions of the vessel wall 70 which are less distended. The internal space 68 of the toroidal encasement member 66 may then be inflated by introduction of a fluid to the internal space. The methods for inflating the toroidal encasement member 66 are the same as have been previously described with respect to the toroidal collars 50 of the alternative embodiment. Notably, a valve 58 may be formed through the toroidal encasement member for filling the internal space 68 by conduit means as previously described.

In the embodiment shown in FIG. 5, each leg portion 25 has associated therewith a toroidal collar 50 encircling the circumference of the leg portion 25 at the lower extremity 44 thereof. The toroidal collars 50 are deployed and inflated in the manner previously described.

Figure 6:
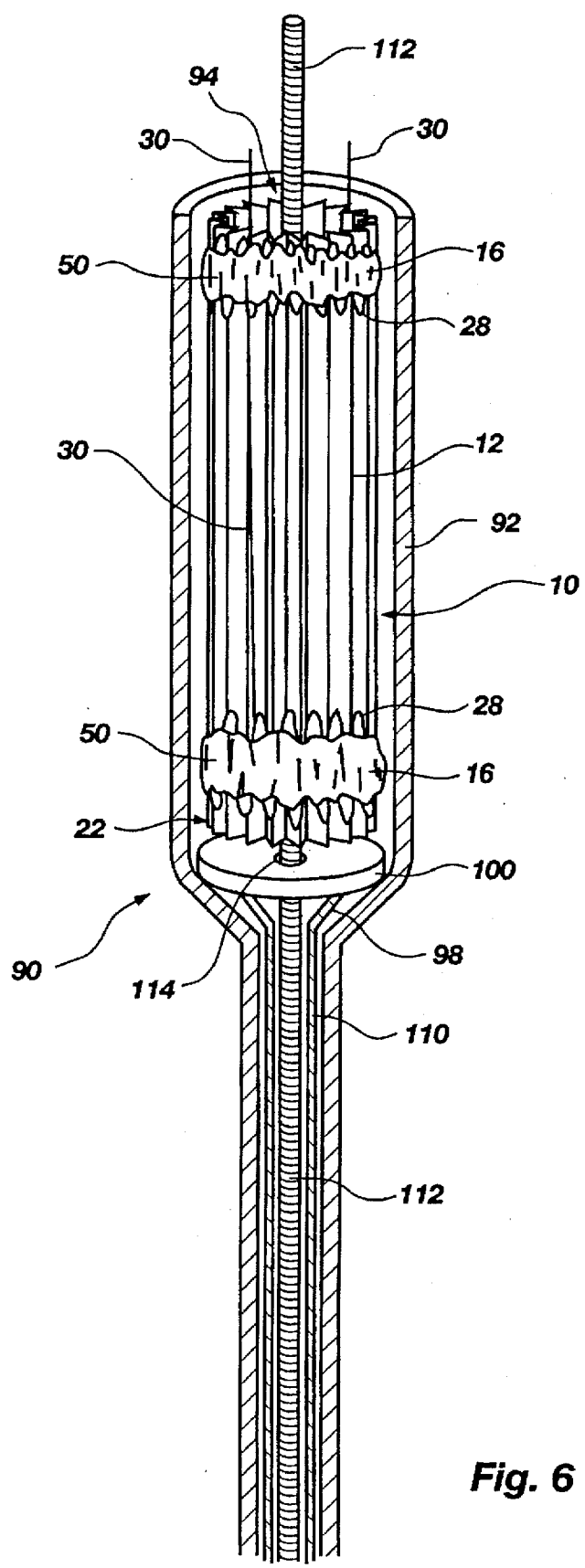
FIG. 6 is a view in cross section of a transporting and deployment structure for positioning the vascular graft into a vessel.

Deployment of the vascular graft 10 may be accomplished in a variety of ways. Generally, however, transportation structure may be used to retain the vascular graft 10 in a pre-deployment state and to move the vascular graft 10 through the arterial system to the area of deployment. One example of a structure for transporting and deploying the vascular graft is shown in FIG. 6. The transportation structure 90 includes a flexible capsule 92 configured and sized to receive and retain the vascular graft 10 in a circumferentially compressed state, as shown. The capsule 92 may be formed as a solid tube of flexible material which allows the capsule 92 to bend freely while being passed through the sometimes tortuous arterial system. The capsule 92 may alternatively be formed from a continuous coil of material which imparts flexibility to the structure. Alternatively, the capsule 92 may be in the form of a tear-away sheath which is removable from about the vascular graft 10 once the graft 10 is in position within the vessel. Other transportation structures exist in addition to these which are also equally suitable.

The capsule 92 has an open proximal end 94 and an enclosed distal end 96. The vascular graft 10 is positionable within the capsule 92 in a circumferentially compressed state as shown. The tubular body 12, the circumferential support structures 28 and the attachment means 16, shown here as toroidal collars 50, are each compressed to fit within the capsule 92. A stabilizer rod 98 is positioned at the distal end 96 of the capsule 92 and is positioned adjacent the distal end 22 of the vascular graft 10. The stabilizer rod 98 may generally comprise a platform 100 and pusher rod 110, and may be structured to allow the placement of a guide wire 112 or a sheath through the capsule 92 and through the compressed vascular graft 10 as shown. A guide wire 112 may facilitate placement of the vascular graft 10 in the vessel and may be positionable relative to the graft 10 and capsule 92 in any appropriate manner. Alternatively however, means other than a guide wire 112 may be used to facilitate deployment of the graft 10, or no guidance means may be necessary or desirable for deployment.

Figure 7D:
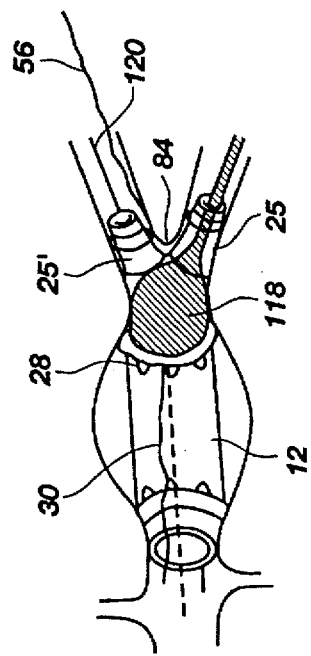
FIGS. 7A–F illustrate deployment of the intraluminal vascular graft within a diseased vessel.

The stabilizer rod 98 may preferably be constructed with a hollow tube, such as the pusher rod 110, so that fluid substances may be passed therethrough into the vessel, as described further below. The platform 110 is also formed with a central opening 114 to accommodate passage of the guide wire 112 and fluid therethrough. Once the vascular graft 10 is correctly positioned within the vessel 76 at the disease site, the stabilizer rod 98 maintains the vascular graft 10 in place within the vessel 76 while the capsule 92 is withdrawn from about the graft 10, as shown in FIGS. 7A and 7B. When a tear-sheath is used as the capsule 92, a line or similar means may be used to initiate tearing of the sheath and the sheath may be withdrawn from the artery 80.

Upon removal of the capsule 92 from around the vascular graft 10, the compressive force provided by the capsule 92 to keep the vascular graft 10 compressed is removed. As a result, the circumferential support structures 28 instantaneously expand and the vascular graft 10 expands radially outward from a central longitudinal axis. Expansion of the vascular graft 10 may be aided by various means if necessary.

Figure 7E:
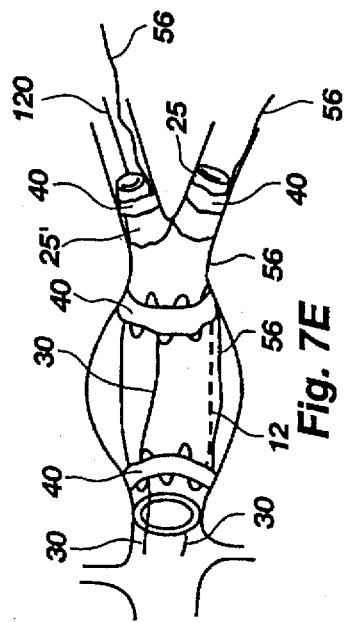
Figure 7F:
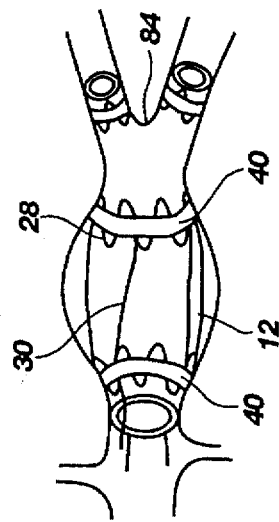
Figure 7A:
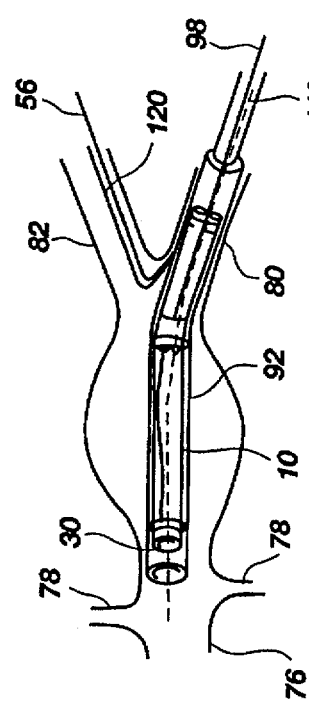
Figure 7B:
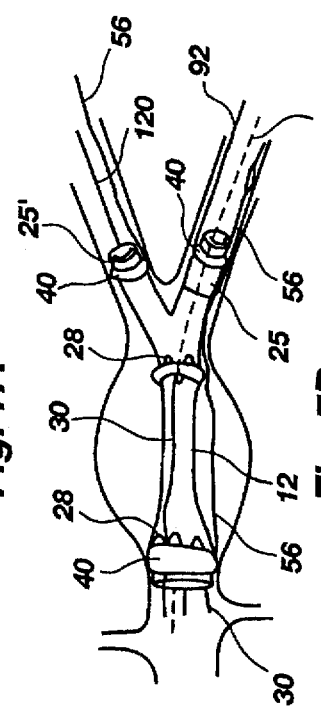
Figure 7C:
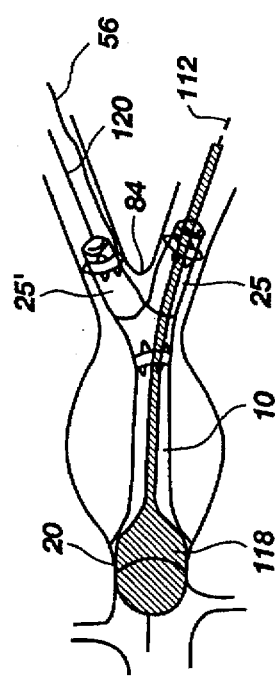

For example, as shown in FIG. 7C, a balloon catheter 118 may be introduced into the femoral artery (not shown), then into the fight iliac artery 80 and through the vascular graft 10 after the stabilizer rod 98 has been retrieved from within the vascular graft 10. Placement of the balloon catheter 118 may be facilitated by the guide wire 112 which remains positioned within the vascular graft 10. The balloon catheter 118 is positioned at the proximal end 20 of the vascular graft 10 and fluid, such as air or saline, is introduced into the balloon 118. Expansion of the balloon 118 forces the vascular graft 10 outwardly to the maximum circumferential limit of the circumferential support structures 28. As the balloon 118 is withdrawn from inside the vascular graft 10, the expanded balloon 118 sequentially expands the more distal regions of the vascular graft 10 until the vascular graft 10 is fully expanded, as shown in FIGS. 7C and 7D. The balloon catheter 118 is then retrieved through the iliac artery 80. The guide wire 112 is also removed. Alternative expansion means may comprise introducing a hydraulic force into the center of the vascular graft 10. For example, a bolus of saline solution may be introduced into the inside of the vascular graft 10 by way of the hollow pusher rod 110 of the stabilizer rod 98. The hydraulic force provided by the saline facilitates outward expansion of the vascular graft 10.

Following removal of the capsule 92, the toroidal collars 50 (or toroidal encasement member, when used) may be enlarged or inflated by introducing a fluid through inflation conduits 56 connected to each toroidal collar 50, as shown in FIG. 7E. Once inflated, the inflation conduits 56 are detached from the toroidal collars 50, as previously described, and the inflation conduits 56 are removed from the vessel 76 and the patient's body.

The procedure for positioning, deploying and expanding the vascular graft 10 within the vessel 76 described hereinabove is appropriate for positioning single tubular grafts 10, as illustrated in FIG. 2, and for positioning tubular grafts 10 having a single leg portion 25 which is positioned within the iliac artery 80 through which the device is transported. However, when the device includes either a second shortened leg portion 25 or two leg portions 25, additional procedures must be performed to bring the second leg portion 25' (FIGS. 7A–F) over from the iliac artery 80 through which the device is transported so that the second leg portion 25' may be positioned within the other branching vessel 82.

A first method for positioning the second leg portion 25' into the other iliac artery 82 is illustrated in FIGS. 7A–7E where a catheter or guide wire 120 is inserted into the femoral artery (not shown) which is not used for transport of the device to the vessel 76. The guide wire 120 is inserted in the arterial system prior to insertion of the intraluminal vascular graft 10 into the arterial system. The guide wire 120 is directed through the left iliac artery 82 to the point of bifurcation of the vessel 76. The guide wire 120 is then passed over the cusp 84 and is directed through the right iliac artery 80 through which the device will ultimately be transported.

The guide wire 120 is passed out of an incision formed through the right femoral artery (not shown) through which the intraluminal vascular graft 10 will be positioned. The end of the guide wire 120 is sutured to the second leg portion 25', or otherwise attached in a manner which may be easily broken or severed when necessary. An inflation conduit 56 may also be attached at the same time for later inflation of the toroidal collar 50 attached to the second leg portion 25' in the manner previously described. The capsule 92 containing the vascular graft 10 is then inserted into the right femoral artery and iliac artery 80 as described previously above.

While the stabilizer rod 98 is still in place maintaining the vascular graft 10 in position within the vessel 76, the guide wire 120 is withdrawn from the left iliac artery 82 thereby bringing the second leg portion 25' over the cusp 84 and into the left iliac artery 82. At this point, expansion means may be introduced into the left femoral and iliac arterial route to provide expansion of the second leg portion 25' if necessary. The toroidal collar 50 associated with the second leg portion 25' may also be inflated. Once positioned and expanded, the guide wire 120 is detached from the second leg portion 25' and the guide wire 120 is removed from the arterial system. The inflation conduit 56 is also removed. Alternatively, a long suture line which is secured to the second leg portion in the manner previously described may be detached from the second leg portion 25', and the suture line removed from the left femoral artery.

Alternatively, the vascular graft 10 may be deployed in the vessel 76 first, as described previously, and then the guide wire 120 is introduced into the left femoral artery and left iliac artery 82. The guide wire 120 is advanced through the left iliac artery 82 to the cusp 84 of the bifurcation. The guide wire 120 is urged across the cusp 84 and down the right iliac artery 80. The guide wire 120 is formed with a hook or other device capable of grasping the second leg portion 25'. The second leg portion 25' is secured by the hook and the guide wire 120 is withdrawn, urging the second leg portion 25' over the cusp 84 and into the left iliac artery 82. The hook or the guide wire 120 is thereafter disengaged from the second leg portion 25' and the guide wire 120 is removed from the left iliac artery 82 and left femoral artery. Expansion means may thereafter be introduced into the right femoral artery and right iliac artery 80 as previously described.

Alternatively to the foregoing deployment procedures, the second leg portion 25' may be deployed in the left iliac artery 82 by compressing the second leg portion 25' against the tubular body 12 in the area of the expandable distal support 32, and as the capsule 82 is removed from about the vascular graft 10, and the distal support 32 expands, the second leg portion 25' moves independently into the left iliac artery 82. This deployment method may be particularly suitable in an embodiment where the second leg portion 25' is shortened.

The intraluminal vascular graft disclosed herein may be used in the repair of any diseased vessel, including but not limited to the repair of aneurysms and partial or full stenoses or blockages. The vascular graft may be deployed in any vessel, whether straight or bifurcated. The concept may be adapted to virtually any type or configuration of vascular repair in either humans or other animals. The present invention is designed to prevent extraluminal channel formation (perigraft leakage), and to prevent enlargement of the proximal and distal extremities of the aneurysm. The structure of the invention may be modified accordingly to meet the demands of the particular application. Hence, reference herein to specific details of the illustrated embodiments is by way of example and not by way of limitation. It will be apparent to those skilled in the art that many additions, deletions and modifications to the illustrated embodiments of the invention may be made without departing from the spirit and scope of the invention as defined by the following claims.

What is claimed is:

1. An intraluminal vascular graft structure comprising:
    a flexible tubular body formed from a biocompatible material, said tubular body having an open proximal end, an open distal end and a longitudinal axis oriented between said open ends, said tubular body being compressible transverse said longitudinal axis for providing a first reduced circumference thereabout relative to a second expanded circumference;
    a compressible frame positioned against said flexible tubular body and oriented both along said longitudinal axis and around said circumference of said flexible tubular body, said frame being structured to support said flexible tubular body at said distal end and from said distal end toward said proximal end; and
    attachment means positioned circumferentially about said flexible tubular body and having pores on the surface thereof sufficient for promoting ingrowth of tissue into said
    attachment means, said attachment means being structured to alternately assume said first reduced circumference and said second expanded circumference in tandem with said flexible tubular body.

2. The intraluminal vascular graft structure of claim 1 wherein said compressible frame comprises circumferential support structures oriented about at least a portion of said circumference of said flexible tubular body and longitudinal support structures oriented parallel to said longitudinal axis, said circumferential support structures being radially expandable.

3. The intraluminal vascular graft structure of claim 2 wherein said attachment means is further treated with a substance which enhances ingrowth of tissue into said pores of said attachment means.

4. The intraluminal vascular graft structure of claim 3 wherein said attachment means includes a first collar of material positioned about the circumference of said flexible tubular body at said open proximal end, said collar being porous.

5. The intraluminal vascular graft structure of claim 4 wherein said attachment means further includes a second collar of material positioned about the circumference of said flexible tubular body at said open distal end, said collar being porous.

6. The intraluminal vascular graft structure of claim 3 wherein said attachment means is made of porous and textured polyurethane.

7. The intraluminal vascular graft structure of claim 2 wherein said longitudinal support structures extend beyond said open proximal end of said flexible tubular body.

8. The intraluminal vascular graft structure of claim 7 wherein said attachment means are positioned proximate said circumferential support structures.

9. The intraluminal vascular graft structure of claim 8 wherein said attachment means are treated with a substance selected to enhance the ingrowth of tissue into said pores.

10. The intraluminal vascular graft structure of claim 9 wherein said flexible tubular body is treated with a substance selected to promote an inflammatory response in surrounding tissue to promote incorporation of said flexible tubular body into a surrounding vessel environment.

11. The intraluminal vascular graft structure of claim 3 wherein said compressible frame is treated with a radio-opaque substance to facilitate determination of placement of said intraluminal vascular graft within a vessel.

12. The intraluminal vascular graft structure of claim 11 wherein said attachment means is treated with a radio-opaque substance selected to facilitate determination of placement of said intraluminal vascular graft within said vessel.

13. The intraluminal vascular graft structure of claim 1 wherein said flexible tubular body further includes at least one tubular leg portion extending from said open distal end.

14. The intraluminal vascular graft structure of claim 13 wherein said at least one leg portion includes a compressible frame structure to support said at least one tubular leg portion with a vessel.

15. The intraluminal vascular graft structure of claim 14 wherein said at least one tubular leg portion further includes attachment means positioned about the circumference of said at least one tubular leg portion, said attachment means having pores for promoting ingrowth of tissue into said attachment means.

16. An intraluminal vascular graft structure comprising:
    a flexible tubular body formed from a biocompatible material and sized for intraluminal positioning, said tubular body having an open proximal end, an open distal end and a longitudinal axis oriented between said open ends, said tubular body being compressible transverse said longitudinal axis for providing a first reduced circumference thereabout relative to a second expanded circumference;
    a compressible frame positioned against said flexible tubular body and oriented both along said longitudinal axis and around said circumference of said flexible tubular body, said frame being structured to support said flexible tubular body at said distal end and from said distal end upwardly toward said proximal end; and
    attachment collars positioned circumferentially about said flexible tubular body in proximity to said distal end and said proximal end for facilitating ingrowth of cellular matter into said attachment collars to promote incorporation into a vessel wall.

17. The intraluminal vascular graft structure of claim 16 wherein said attachment collars are formed of a material having porosity sufficient to promote ingrowth of cellular matter thereinto to facilitate incorporation of said attachment means into said vessel wall.

18. The intraluminal vascular graft structure of claim 16 wherein said attachment collars are treated with material which renders the surface of said attachment collars sufficiently porous to promote ingrowth of cellular matter thereinto to facilitate incorporation of said attachment collars into said vessel wall.

19. An intraluminal vascular graft structure comprising:
    a flexible tubular body formed from a biocompatible material, said tubular body having an open proximal end, an open distal end and a longitudinal axis oriented between said open ends, said tubular body being compressible transverse said longitudinal axis for providing a first reduced circumference thereabout relative to a second expanded circumference;

a compressible frame positioned against said flexible tubular body and oriented both along said longitudinal axis and around said circumference of said flexible tubular body, said frame being structured to support said flexible tubular body at said distal end and from said distal end upwardly toward said proximal end; and at least one toroidally-shaped attachment means positioned circumferentially about said flexible tubular body and having pores on the surface thereof sufficient for promoting ingrowth of tissue into said attachment means.

20. The intraluminal vascular graft structure of claim 19 wherein said at least one toroidal attachment means includes a first collar having an internal, inflatable space formed therein, said first collar being positioned about the circumference of said flexible tubular body at said open proximal end, said first collar being at least partially porous.

21. The intraluminal vascular graft structure of claim 19 wherein said toroidal attachment means further includes a second collar having an internal, inflatable space formed therein, said second collar being positioned about the circumference of said flexible tubular body at said open distal end, said second collar being at least partially porous.

22. The intraluminal vascular graft structure of claim 19 wherein said toroidal attachment means comprises a toroidal encasement member having an internal, inflatable space formed therein, said toroidal encasement member extending from said open proximal end to said open distal end and being at least partially porous.

* * * * *

UNITED STATES PATENT AND TRADEMARK OFFICE
CERTIFICATE OF CORRECTION

PATENT NO. : 5,693,088
DATED : December 2, 1997
INVENTOR(S) : Lazarus

It is certified that error appears in the above-identified patent and that said Letters Patent is hereby corrected as shown below:

In column 2, line 64, change "dose" to --close--;
In column 12, line 8, change "read fly" to --readily--;
In column 15, line 26, change "extends" to --external--;
In column 17, line 22, change "fight" to --right--.

Signed and Sealed this

Twenty-fifth Day of May, 1999

Attest:

Q. TODD DICKINSON

*Attesting Officer*  *Acting Commissioner of Patents and Trademarks*